United States Patent [19]
Hiltebrandt et al.

[11] Patent Number: 5,112,346
[45] Date of Patent: May 12, 1992

[54] RETROGRADE CUTTING HOOK PUNCH

[75] Inventors: Siegfried Hiltebrandt, Knittlingen; Andreas Dingler, Birkenfeld; Ernst Falk, Sternenfels-Diefenbach, all of Fed. Rep. of Germany; Martin F. Fischmeister, Linz, Austria

[73] Assignee: Richard Wolf GmbH, Knittlingen, Fed. Rep. of Germany

[21] Appl. No.: 509,666

[22] Filed: Apr. 16, 1990

[30] Foreign Application Priority Data

Jun. 8, 1989 [DE] Fed. Rep. of Germany ....... 3918720

[51] Int. Cl.⁵ ............................................. A61B 17/32
[52] U.S. Cl. ...................................... 606/170; 30/251
[58] Field of Search ............... 606/167, 170, 174, 205; 30/249–251; 604/22, 4–6; 128/750, 751, 749

[56] References Cited

U.S. PATENT DOCUMENTS

| | | | |
|---|---|---|---|
| 2,668,537 | 2/1954 | Kapp | 606/174 |
| 2,691,370 | 10/1954 | Wallace | 606/170 |
| 4,662,371 | 5/1987 | Whipple | 128/312 |
| 4,763,669 | 8/1988 | Jaeger | 128/751 |
| 4,944,093 | 7/1990 | Falk | 30/251 |

FOREIGN PATENT DOCUMENTS

| | | |
|---|---|---|
| 3303349 | 8/1984 | Fed. Rep. of Germany . |
| 3523022 | 3/1986 | Fed. Rep. of Germany . |
| 3614736 | 11/1987 | Fed. Rep. of Germany . |
| 8712271 | 3/1988 | Fed. Rep. of Germany . |
| 8810968 | 12/1988 | Fed. Rep. of Germany . |
| 1037403 | 9/1953 | France . |
| 2161707 | 1/1986 | United Kingdom ................ 606/170 |

*Primary Examiner*—C. Fred Rosenbaum
*Assistant Examiner*—William Lewis
*Attorney, Agent, or Firm*—Panitch Schwarze Jacobs & Nadel

[57] ABSTRACT

A retrograde cutting hook punch for arthroscopy is so designed that two ends of a fixed and a pivotable jaw member which are remote from the axis of pivot of the pivotable jaw member are laterally positioned at an angle to the longitudinal axis of the forceps, the pivotable jaw member, which is pivotable between limits set by two abutments, having an axially directed part which is guided to pivot in a longitudinal slot in the fixed jaw member, said axially directed part being provided with a downwardly open longitudinal slot to receive a traction and thrust rod for actuating the pivotable jaw member.

4 Claims, 1 Drawing Sheet

RETROGRADE CUTTING HOOK PUNCH

BACKGROUND OF THE INVENTION a) Field of the Invention

The invention is based on a retrograde cutting hook punch in which one jaw member, which is operated by a traction and thrust rod, is mounted to be pivotably movable in a retrograde direction in the distal end of the other jaw member, which is rigidly fixed to the barrel, of the kind known from DE-GM 8 712 271 and GE-OS 35 23 022.

b) Description of the Prior Art

These known instruments which operate in the retrograde direction are used to remove pieces of tissue or even to take away foreign bodies but they are of only limited suitability for arthroscopy because the space available in the knee-joint for inserting cutters through a trocar cannula is only very small and thus permits only a very limited amount of manipulation. Hence a number of different instruments are needed for operations in the knee-joint and it is generally also necessary for a number of incisions to be made.

The main object of the present invention is to enable the major part of an operation in a knee-joint to be dealt with, and above all the critical region of the joint to be operated on all in one procedure, with a single retrograde cutting hook punch, and hence the need for a plurality of incisions in the knee-joint may be avoided.

SUMMARY OF THE INVENTION

To this end, the present invention consists in a retrograde cutting hook punch, in which one jaw member, which is operated by a traction and thrust rod, is mounted to be pivotably movable in a retrograde direction in the distal end of the other jaw member, which is rigidly fixed to the barrel, characterised in that, for performing operations in the knee joint, those two ends of the jaw member which are remote from the axis of pivot of the pivotably mounted jaw member are laterally positioned at an angle to the longitudinal axis of the punch, the pivotable jaw member which is pivotable between limits set by two abutments, having an axially directed part which is pivotable in a longitudinal slot in the fixed jaw member and which is provided with a downwardly open longitudinal slot to receive the traction and thrust rod.

This method of achieving the object makes it possible for the hook punch to be inserted in the knee joint through one incision, in which case it is then possible for complete operations to be carried out on parts of the joint with a single instrument without the need for any special manipulation of the instrument.

With the hook punch according to the invention the possibility exists of performing a meniscal resection and of dealing with the critical region in the knee-joint with virtually no major changes in position, in which case visual monitoring is via a telescope which has been inserted through an incision into the articular cavity, which has been enlarged by distension. This being the case, to avoid any injury in the articular cavity, the instrument is of atraumatic form at its distal end and in the region of the retrograde directed jaw members. Because of its design, the hook punch according to the invention has a form of cutting edge adapted to anatomical conditions, thus making any but the most minor changes of position unnecessary. What is also obtained is high strength for the jaws.

BRIEF DESCRIPTION OF THE DRAWINGS

In order that the invention may be more readily understood, an embodiment thereof will now be described, by way of example, with reference to the accompanying drawings, in which.

DESCRIPTION OF THE PREFERRED EMBODIMENT

Figure 1:
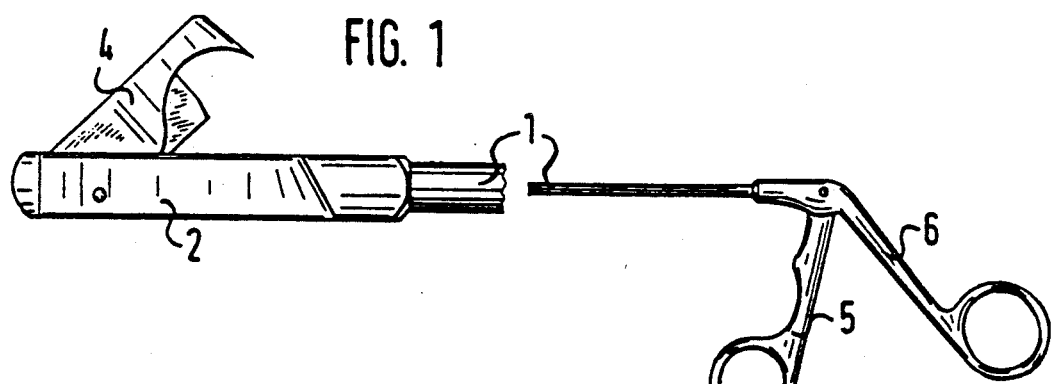
FIG. 1 is a side elevation of a hook punch constructed according to the present invention with a distal end of the instrument shown to an enlarged scale and with its jaws open.
Figure 3:
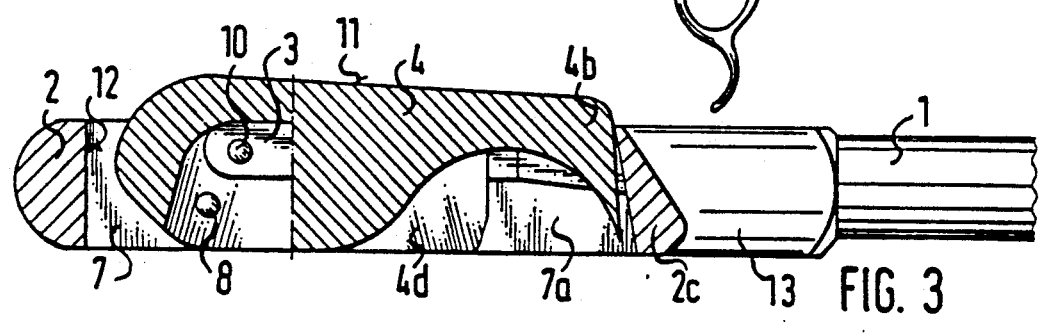
FIG. 3 is a section taken along broken line III—III in FIG. 2.
Figure 4:
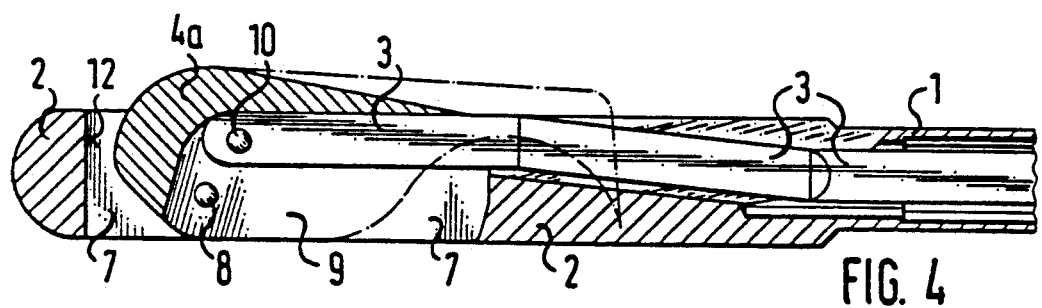
FIG. 4 is a section taken along the longitudinal axis represented by line III-IV in FIG. 2.
Figure 2:
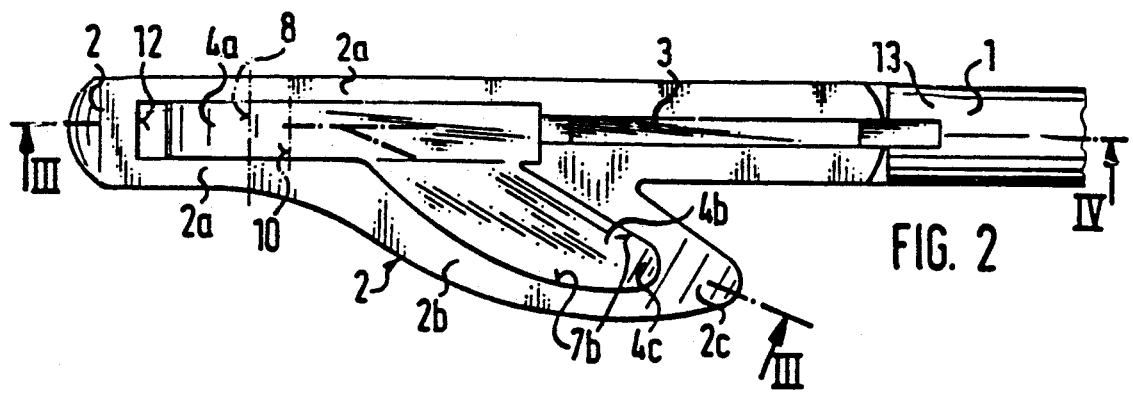
FIG. 2 is an enlarged plan view of the distal end of the hook punch of FIG. 1, but with its jaws closed.

Referring to the drawings, the hook punch comprises a hollow barrel 1 which is provided distally with a fixed jaw member 2 and through which extends a traction and thrust rod 3 for the second, pivotable jaw member 4. The rod 3 is actuated by part 5 of the handle while the second part 6 of the handle is rigidly connected to the proximal end of the (barrel).

The fixed jaw member 2 comprises a straight part 2a extending in the longitudinal direction of the hook punch, which merges into a part 2b which is angled away from the longitudinal axis 13 laterally. The straight part 2a is provided with a longitudinal slot 7, branching off from which at an angle is a part 7a whose upper boundary wall forms the cutting edge 7b of the fixed jaw member, with which the cutting edge of the pivotably jaw member 4 co-operates.

Mounted to pivot about an axis 8 in the straight, axial part 7 of the slot is the axially extending part 4a of jaw member 4, and following on from this axially extending part 4a in a direction approximately parallel to the fixed, angled part 2b of jaw member 2 is a part 4b of jaw member 4, which is likewise angled away laterally. The axially extending jaw member part 4a is provided with a longitudinal slot 9 which opens only downwards and through which extends the distally flattened end of the traction and thrust rod 3, which is hinged to pivotable jaw member 4 at 10. The side faces of the straight, pivotable part are guided directly in the straight part of the longitudinal slot 7 in the fixed jaw member, thus increasing the rigidity of the jaws and preventing the pivotable jaw member 4 from being deflected when cutting through tissue, cartilage or tough matter. The free ends 2c and 4c of the two jaw members 2 and 4 are of atraumatic configuration to prevent injury from occurring when they are inserted into the distended knee-joint.

The hook punch is inserted into a distended knee-joint through an incision while in the closed state, in which state the bottom face of the downwardly open slot 9 in the pivotably jaw member 4 rests on the top face of the flattened part of the traction and thrust rod 3, which acts as an abutment, and prevents jaw member 4 from projecting downwards out of part 7a of the slot in the fixed jaw member 2. To perform an operation, the jaws are opened by actuating them with part 5 of the handle and the traction rod 3 to pivot jaw member 4 as shown in FIG. 1, the width to which the jaws will open being limited by the fact that the top face 11 of jaw member 4 butts against the end-face 12 of the longitudinal slot 7 when the fully open position is reached.

We claim:

1. A retrograde cutting hook punch for performing an operation in a knee joint, comprising a longitudinal axis, a barrel having a proximal end, a distal end and a traction and thrust rod therethrough, a pivotable jaw member and a fixed jaw member, each of the jaw members being located at the distal end of the barrel, the pivotable jaw member, which is operated by the traction and thrust rod, being pivotably movable about a pivot axis in a retrograde direction between a first position wherein the pivotable jaw member abuts the traction and thrust rod and a second position wherein the pivotable jaw member abuts the fixed jaw member, each jaw member having a first portion extending outwardly from the barrel towards the proximal end thereof at an angle to the barrel and the longitudinal axis of the punch, each jaw member having one end remote from the pivot axis of the pivotable jaw member, said first portion of said fixed jaw member including a slot for complementarily receiving the first portion of the pivotable jaw member to form a cutting edge, the pivotable jaw member having an axially directed second portion which is pivotable in a longitudinal slot defined in a second portion of the fixed jaw member, the pivotable jaw member defining a downwardly open longitudinal slot for receiving the traction and thrust rod.

2. A hook punch according to claim 1, wherein the traction and thrust rod is pivotally connected to the pivotable jaw member by a hinge and has an upper face which forms, in a region before the hinge, one of said abutments for the pivotable jaw member in a jaw closed position, and the longitudinal slot in the fixed jaw member has a distal end face which forms the other of said abutments, for an upper face of the pivotable jaw member, to determine how wide the pivotable jaw member can open.

3. A hook punch according to claim 2, wherein the fixed and pivotable jaw members have free ends which are of atraumatic form.

4. A hook punch according to claim 1, wherein the fixed and pivotable jaw members have free ends which are of atraumatic form.

* * * * *